United States Patent [19]  [11] 4,353,708
Boré et al.  [45] Oct. 12, 1982

[54] EVALUATION OF THE STATE OF CHANGE OF KERATIN FIBERS

[75] Inventors: Pierre Boré, Montfermeil; Arnaud De Labbey, Aulnay-Sous-Bois, both of France

[73] Assignee: L'Oreal, Paris, France

[21] Appl. No.: 55,213

[22] Filed: Jul. 6, 1979

[30] Foreign Application Priority Data

Jul. 13, 1978 [FR] France .................................. 78 20975
Jun. 8, 1979 [FR] France .................................. 79 14791

[51] Int. Cl.$^3$ ............................................. G01N 31/00
[52] U.S. Cl. ................................... 23/230 B; 23/230 M
[58] Field of Search ............ 23/230 R, 230 B, 230 M; 252/408; 422/55, 56, 68, 69

[56] References Cited

U.S. PATENT DOCUMENTS 3,592,603 7/1971 Miller et al. ......................... 252/408

FOREIGN PATENT DOCUMENTS 922606 4/1963 United Kingdom .................. 422/56

OTHER PUBLICATIONS

Finkelstein, P. et al., American Perfumer and Cosmetics, vol. 81, Sep. 1966, pp. 39–40, 42.
Chemical Abstracts, vol. 65, 1966, Abstract No. 16786h, Laden, K. et al., "The Modification of the Ionic Character of Hair".
Chemical Abstracts, vol. 48, 1962, Abstract No. 11833g, Underwood, D. L. et al., "The Kinetics of the Absorption and Desorption of Single Ions by Keratin Fibers".
Neurath, Hans, The Proteins, vol II, Academic Press, N.Y., 1964, pp. 249–250.

Primary Examiner—Frank W. Lutter
Assistant Examiner—Chris Konkol
Attorney, Agent, or Firm—N. Jerome Rudy

[57] ABSTRACT

A process for evaluating the ionic state of the surface of keratin fibers, especially human hair, which comprises, taking at least one sample of fibers from the fibers to be evaluated, contacting the sample with an acidic solution of at least one acidic basic dyestuff, assessing what, if any, change in the color of the solution has taken place and attributing the ionic state to the surface of the fibers accordingly.

21 Claims, No Drawings

EVALUATION OF THE STATE OF CHANGE OF KERATIN FIBERS

DESCRIPTION

This invention relates to the evaluation of the state of change of keratin fibres, especially human hair.

It is known that, in order to advise and direct the choice of a customer towards hair-treatment products which are capable of being most satisfactory, it is desirable to know precisely the state of the hair in question since various treatments which it may have undergone previously have an effect on it. Similarly, it can be useful for the expert to check during various cosmetic treatments such as permanent-waving, bleaching and coloring treatments whether the applications and the rinses have been carried out satisfactorily, by evaluating certain characteristics of the hair.

The present invention is based on the observation that the hair can, in effect, exhibit three different ionic states, depending on the previous cosmetic treatments which have been applied to it, namely:

the negative, hereinafter symbolized as (−), ionic state, in particular in the case of hair which has been bleached without any subsequent treatment;

the positive, hereinafter symbolized as (+), ionic state, in particular in the case of hair to which to cationic polymer has been applied, whether or not the hair has been bleached beforehand; and the "neutral" state, in the case of natural hair which has not undergone any treatment capable of modifying its ionic charge.

The object of the present invention is to describe a colorimetric test based on the difference in affinity exhibited by acidic, basic or neutral dyestuffs with respect to hair in a given ionic state and at a given pH. This colorimetric test should be easy to carry out and be such that any person, even someone unskilled in laboratory technique, can evaluate the ionic state of the hair, either in order to check, during a cosmetic treatment, that the application and the rinsing have been carried out successfully, or in order to direct customers towards the most suitable cosmetic products. An additional aim is to produce a laboratory colorimetric test which makes it possible not only to evaluate the ionic state (positive, negative or neutral) of the hair but also to determine, precisely and reliably, the degree of charge on the hair.

The present invention provides a process for evaluating the (−) ionic state, the (+) ionic state or the neutral ionic state of the surface of keratin fibers, and in particular of human hair, to which reference will be made in the following discussion. The neutral ionic state is herein defined as the state of natural hair which has not undergone any treatment capable of modifying its ionic charge.

The present process comprises taking at least one sample of hair from a volume of hair to be evaluated, then contacting the sample with an acidic solution containing at least one acidic or basic dyestuff, and finally assessing whether or not the color of the solution has changed. When carrying out the process according to the invention as a simplified test, the variation in coloration is assessed visually. On the other hand, when the process according to the invention is applied as a laboratory test, the variation in coloration, and hence the exhaustion of the dyestuff from the solution placed in contact with the hair, can be determined spectrophotometrically.

According to the invention, the contact time between the solution of dyestuff(s) and the sample of hair is preferably short in order, in particular, to avoid complications due to the penetration of the dyestuff into the hair. Contact times of, say, 30 to 3 minutes are advantageously used but these times are not essential.

In order to obtain reliable results, it is important to clean the hair appropriately with a washing solution based on a non-ionic surface-active agent which is preferably non-foaming but which has sufficient detergent power.

The sample of hair can be taken by any appropriate means. If several samples of hair are taken, this should be carried out so that the samples are of essentially the same weight. In order to carry out the invention as a simplified test, the solution of dyestuff(s) placed in contact with the sample of hair is preferably between 0.25 cm$^3$ and 1 cm$^3$; the weight of the samples of hair is 10 to 50 mg; the concentration of dyestuff(s) in the solution is generally 0.005% to 0.02% by weight.

In a first embodiment of the invention, as a simplified test, at least one sample of hair is placed in contact with a single solution of acid pH, of two dyestuffs giving different colorations, these two dyestuffs being chosen so as to permit two different changes in the initial coloration of the solution, namely one change in the coloration in the presence of hair in the (+) ionic state and another change in the presence of hair in the (−) ionic state, the initial coloration being maintained in the presence of natural hair (neutral ionic state). Preferably, one of the two dyestuffs in the mixture is an acidic dyestuff whilst the other is a basic dyestuff.

As an example of such a mixture of acid pH of an acidic dyestuff and a basic dyestuff, there may be mentioned 1-N-(γ-aminopropyl)-amino-4-N'-(methyl)-aminoanthraquinone (a basic dyestuff given in Table II) mixed with "Kiton Fast Red R", number 14.905 in the "Color Index" (an acidic dyestuff given in Table I).

If it is desired to determine only the ionic state of the hair and not the degree of charge thereon, it suffices, in this first embodiment, to take a single sample of hair; this sample is placed in contact with the solution of the two dyestuffs in order to evaluate the sign of the ionic state of the hair. The pH of the soluton of the two dyestuffs is advantageously from 0.5 and up to (but not including) 7 and is preferably about 1.8.

In a second embodiment of the invention as a simplified test, the (+), (−) or neutral ionic state of the hair is determined using two solutions of dyestuffs of acid pH, each of which is placed in contact with at least one sample of the hair to be tested. One of the two solutions, which contains at least one acidic dyestuff, is capable of changing its coloration in the presence of hair in the (+) ionic state, whilst the second solution, which contains at least one basic dyestuff, is capable of changing its coloration in the presence of hair in the (−) ionic state; the pH of these two solutions is adjusted so that the initial coloration of each solution remains unchanged in the presence of natural hair (neutral ionic state). The pH of the solution which contains at least one basic dyestuff is generally from 0.5 up to 7 and is preferably about 1.8. The solution which contains at least one acidic dyestuff is generally used at a pH of 1 up to 7 and preferably at a pH of about 3.5.

In this second embodiment, the (+), (−) or neutral ionic state of the hair can be determined using two samples of hair placed in contact with the two colored solutions mentioned above. However, if it is desired to evaluate not only the ionic state of the hair but also the degree of charge thereon, the colored solution based on an acidic dyestuff, which contains the sample of hair, can be compared against a calibrated scale for the same colored solution; likewise, the colored solution based on a basic dyestuff, which contains a sample of hair, can be compared against a calibrated scale for the same colored solution.

In the simplified test, the (+), (−) or neutral ionic state of the hair can be determined by preparing two samples for analysis, the one containing the colored solution based on an acidic dyestuff, placed in contact with a sample of the hair to be tested, and the other containing the colored solution based on a basic dyestuff, placed in contact with another sample of hair. If the expert does not observe any decoloration of the two samples for analysis, he or she can deduce therefrom that the hair tested is natural hair in the neutral ionic state; if, on the other hand, the expert observes a decoloration or a change in the sample for analysis, which contains the solution based on an acidic dyestuff, he or she can deduce therefrom that the hair is in the (+) ionic state; finally, if the expert observes a decoloration or a change in the sample for analysis, which contains the solution based on a basic dyestuff, this will mean that the hair tested is in the (−) ionic state.

According to a first variant, the solution of dyestuff(s) intended to demonstrate the (+) ionic state of the hair, in the simplified test, contains a single acidic dyestuff. Preferred acidic dyestuffs are listed in Table I.

According to a second variant, the solution of dyestuff(s) intended to demonstrate (+) ionic state of the hair, in the simplified test, contains a mixture of two acidic dyestuffs giving different colorations. As an example of a mixture of two acidic dyestuffs, there may be mentioned a mixture of phthalocyanine (number 74.220 in the "Color Index"), which gives a blue coloration, and "Kiton Fast Red R" (number 14.905 in the "Color Index"). The mixture of these two dyestuffs is blue-violet. This coloration is maintained in the presence of untreated natural hair (neutral ionic state); the mixture changes from blue-violet to red-pink in the presence of hair which is in the (+) ionic state.

According to a third variant, the solution of dyestuff(s) intended to demonstrate the (+) ionic state of the hair, in the simplified test, contains both an acidic dyestuff and a neutral dyestuff. Suitable neutral dyestuffs are indicated in Table III. In order to prepare such colored solution, a neutral red dyestuff for example 3-nitro-4-N-(β-hydroxyethyl)-aminophenol (mentioned in Table III without a "Color Index" number), can be mixed with "Violet Ext D and C" (Table I). The color of the mixture is violet. If the hair is in a neutral state, the coloration of the mixture remains violet; on the other hand, if the hair is in the (+) ionic state, the mixture changes from violet to red.

According to a first variant, the solution of dyestuff(s) intended to demonstrate the (−) ionic state of hair, in the simplified test, contains a single basic dyestuff. Preferred basic dyestuff are listed in Table II.

According to a second variant, the solution of dyestuff(s) intended to demonstrate the (−) ionic state of the hair, in the simplified test, contains two basic dyestuffs giving different colorations. A suitable mixture is a mixture of "Astracyanine B" (number 42.705 in the "Color Index"), which gives a blue coloration, and "Deorline Brilliant Red 4G". The initial coloration of the mixture is violet; this mixture changes from violet to red in the presence of hair in the (−) ionic state (for example bleached hair).

According to a third variant, the solution of dyestuff(s) intended to demonstrate the (−) ionic state of the hair, in the simplified test, contains both a basic dyestuff and a neutral dyestuff giving different colorations. As an example, there may be mentioned 2-nitro-para-phenylenediamine (a neutral yellow dyestuff shown in Table III) mixed with 1-N-(γ-aminopropyl)-amino-4-N′-(methyl)-aminoanthraquinone (a basic dyestuff given in Table II). The coloration of the mixture is green. This coloration remains green in the case of hair which is in a neutral ionic state. On the other hand, the mixture changes from green to yellow when it is placed in contact with hair which is in the (−) ionic state.

If a colored solution containing either a single basic dyestuff or a single acidic dyestuff is used, the (+) or (−) ionic state of the hair is determined not by observing a change in the initial coloration but by observing a decoloration, since, for example, placing the solution which contains the acidic dyestuff in contact with hair in the (+) ionic state results in an adsorption of the dyestuff on the surface of the hair and hence in a reduction in the amount of acidic dyestuff in the solution. Therefore, the concentration of dyestuff in the solution is chosen so that the sample of hair used can substantially exhaust the dyestuff from the solution in the case of a maximum corresponding ionic state. In order to make the decoloration easier to observe, it is advantageous to compare the solution of dyestuff which contains a sample of hair with a control solution of the same dyestuff.

When carrying out the invention as a laboratory colorimetric test, in which the exhaustion of the dyestuff from the solution placed in contact with the sample of hair is determined by spectrophotometry, a solution of acid pH, containing an appropriate acidic dyestuff is prepared in order to demonstrate the degree of (+) charge on the hair. The acidic dyestuff "Violet Ext D and C" is preferably used. The pH of the solution of the acidic dyestuff "Violet Ext D and C" is about 3.5.

In order to demonstrate the degree of (−) charge in the laboratory test, a solution of acid pH, containing a single appropriate basic dyestuff is prepared. The basic dyestuff "Codex Methylene Blue" is preferably used. The solution of the dyestuff "Codex Methylene Blue" has a pH of about 1.8.

The following tests further illustrate the present invention.

In the simplified colorimetric test according to the second embodiment of the invention, samples of hair to be tested are placed in contact with two colored solutions, one of which makes it possible to determine the (−) ionic state and the other of which makes it possible to determine the (+) ionic state. Typically one of the two solutions contains only "Codex Methylene Blue" (a basic dyestuff indicated in Table II) and the second solution contains only "Red No. 4 F D C" (an acidic dyestuff indicated in Table I); the basic dyestuff is used at a pH of 1.8 and the acidic dyestuff is used at a pH of 3.5. The samples of hair are taken from different batches of hair; the hair is either natural, that is to say it has not undergone any treatment capable of modifying the ionic charge thereon, or it has been subjected beforehand to a treatment, such as a permanent-waving, bleaching or dyeing treatment, involving a cationic polymer which has modified the ionic state of the hair.

A degree of ionic charge which is considered to be a maximum for hair is defined in the following manner:

in the case of (+) charged hair, the maximum state of charge corresponds to bleached hair to which 2 to 3% by weight (relative to the weight of the hair) of a cationic polymer has been fixed;

in the case of (−) charged hair, the maximum state of charge corresponds to strongly bleached hair having an alkaline solubility (A.S.) of 25 to 30%.

An adsorption scale from 0 to 100% is defined for each dyestuff. The value 0 corresponds to the case where the dyestuff is placed in contact with a sample of untreated natural hair. The value 100% on the scale corresponds to the case where the dyestuff is placed in contact with hair having a maximum corresponding degree of charge, the volume of the dose of solution, and the concentration of dyestuff therein, being chosen so that the sample of hair having a maximum charge exhausts the solution and leads to a virtually complete decoloration thereof. This result can be obtained by using 25 mg samples of towel-dried hair, 0.5 cm$^3$ of solution with a concentration, by weight, of 0.01% in the case of methylene blue and 0.01% in the case of "Red No. 4 F D C".

It is then possible to prepare a colorimetric calibration scale comprising:

a control solution at the initial concentration of the solution, this corresponding to zero adsorption (uncharged hair);

a solution exhausted at the end of the test (2 minutes) by a sample of hair having a maximum charge; and at least one solution corresponding to an intermediate adsorption level (for example a solution with 50% adsorption).

The procedure used is as follows:

The sample of hair (25 mg of towel-dried hair) is introduced into a solution, which, after shaking for about 2 minutes, is compared with three calibrated solutions of the same dyestuff, corresponding to an adsorption of 0, 50 and 100%. The results obtained are summarized in the two tables which follow.

(a) In the case of the acidic dyestuff:

| Type of hair | Fixing of the dyestuff in 2 minutes |
| --- | --- |
| Natural hair | 0% |
| Bleached hair (A.S.26)* | 0% |
| Permanent-waved natural hair | 50% |
| Permanent-waved bleached hair | 50% |
| Natural hair treated with cationic polymers | 100% |
| Bleached hair treated with cationic polymers | 100% |

*Alkaline solubility of 26%
(Conditions for determining the alkaline solubility: 500 mg of hair + 40 cm$^3$ of N/10 NaOH solution; 30 minutes at 65° C.)

(b) In the case of the basic dyestuff:

| Type of hair | Fixing of the dyestuff in 2 minutes |
| --- | --- |
| Natural hair | 0% |
| Bleached hair (A.S. 9)* | 50% |
| Bleached hair (A.S. 26) | 100% |
| Permanent-waved natural hair | 0% |
| Permanent-waved bleached hair (A.S. 9)* | 50% |
| Permanent-waved bleached hair (A.S. 26) | 100% |
| Natural hair treated with cationic polymers | 0% |
| Bleached hair (A.S. 9)* treated with cationic polymers | 0% |
| Bleached hair (A.S. 26) treated with cationic polymers | 0% |

*Alkaline solubility of 9%

By means of this colorimetric test, it is possible to categorize the different types of hair according to their (+), (−) or neutral ionic state. The colorimetric test can be refined by increasing the number of calibrated solutions. However, the test can be further simplified since the expert, namely the hairdresser for whom this colorimetric test is more particularly intended, simply needs to know whether the ionic state of the surface of the hair is a (−) state, a (+) state or a neutral ionic state, in order to direct the choice of his or her customers towards the most suitable cosmetic products; for this purpose, the calibrated scale of the acidic or basic dyestuff can simply comprise the control solution of the corresponding dyestuff.

Four Examples of the preparation of solutions of dyestuff(s), which can be used in the simplified colorimetric test according to the second embodiment of the invention, and also one example of the preparation of a solution of dyestuff(s), which can be used in the simplified colorimetric test according to the first embodiment of the invention, are given below.

EXAMPLE 1: Preparation of a colored solution, based on two acidic dyestuffs, for demonstrating the (+) ionic state of the hair Phthalocyanine (number 74.120 in the "Color Index") is mixed at a pH of 3.5 with "Kiton Fast Red R" (number 14.905 in the "Color Index"). The coloration of the phthalocyanine is blue and its concentration in the mixture is 0.01%; the concentration of "Kiton Fast Red R" in the mixture is 0.01%; the contact time with the swatches of hair is about 1 minute; the color of the mixture is blue-violet; this coloration does not change in the presence of untreated natural hair (neutral ionic state). This mixture changes from blue-violet to red-pink when it is in contact with hair which is in a (+) ionic state, for example hair treated with cationic polymers.

EXAMPLE 2: Preparation of a colored solution, resulting from the mixture of an acidic dyestuff and a neutral dyestuff, for demonstrating the (+) ionic state of the hair 3-Nitro-4-N-(β-hydroxyethyl)-aminophenol (a neutral red dyestuff shown in Table III) and "Violet Ext. D and C" (Table I) are mixed at a pH of 3.5. These two dyestuffs are used at a concentration of 0.01%. The color of the mixture is violet. If the hair is in a neutral ionic state, the coloration of the mixture remains violet; on the other hand, if the hair is in a (+) ionic state, the coloration changes to red.

EXAMPLE 3: Preparation of a colored solution, resulting from the mixture of two basic dyestuffs, for demonstrating the (−) ionic state of the hair.

"Astracyanine B" (number 42.705 in the "Color Index") and "Deorline Brilliant Red 4G" are mixed at a pH of 1.8. "Astracyanine B" has an initial blue coloration and its concentration in the mixture is 0.05%, whilst "Deorline Brilliant Red 4G" is used at a concentration of 0.01%. The mixture of these two basic dyestuffs has a violet coloration; the contact time used is 2 minutes; in the presence of untreated natural hair, that is to say hair in the neutral ionic state, the coloration of the mixture remains violet; this mixture changes from violet to red in the case of hair which is in a (−) ionic state, for example bleached hair.

EXAMPLE 4: Preparation of a colored solution, resulting from the mixture of a basic dyestuff and a neutral dyestuff, for demonstrating the (−) ionic state of the hair 2-Nitro-para-phenylenediamine (a neutral yellow dyestuff shown in Table III), at a concentration of 0.01%, and 1-N-(γ-aminopropyl)-amino-4-N'-(methyl)-aminoanthraquinone (a blue basic dyestuff with a primary amine group, shown in Table II), at a concentration of 0.05%, are mixed at a pH of 1.8. The color of the mixture is green; this coloration remains green in the case of hair which is in a neutral ionic state. On the other hand, this coloration changes to yellow in the case of hair in a (−) ionic state.

EXAMPLE 5: Preparation of a colored solution, resulting from the mixture of an acidic dyestuff and a basic dyestuff, for demonstrating the (+), (−) or neutral ionic state of the hair 1-N-(γ-Aminopropyl)-amino-4-N'-(methyl)-aminoanthraquinone (a blue basic dyestuff), at a concentration of 0.075%, is mixed, at a pH of 1.8, with "Kiton Fast Red R" (number 14.905 in the "Color Index"), at a concentration of 0.015%. The contact time used is about 1 minute. The color of the mixture is violet; in the presence of untreated natural hair (neutral ionic state), the coloration of the mixture remains violet; the mixture changes from violet to red in the case of hair in a (−) ionic state, for example bleached hair; this mixture changes from violet to blue in the case of hair in a (+) ionic state, for example hair treated with cationic polymers.

Two laboratory methods are given below, one making it possible to demonstrate the degree of (+) charge on hair and the other making it possible to demonstrate the degree of (−) charge.

EXAMPLE 6: Method for the spectrophotometric determination of the amount of basic dyestuff adsorbed by hair The following reagents are prepared:
(a) Buffer solution of pH 3.5, the composition of which is as follows (per liter of solution):
6.7 g of trisodium citrate
9.2 g of citric acid
1 g of sodium chloride
Water: qsp 1 liter;
(b) Concentrated solution of the dyestuff "Violet Ext D and C" (number 60.730 in the "Color Index"), obtained by dissolving 100 mg of the said dyestuff in 100 cm$^3$ of water; and
(c) Dilute solution of the dyestuff "Violet Ext D and C", obtained by introducing 5 cm$^3$ of the concentrated solution referred to under (b) into a 50 cm$^3$ calibrated flask and by making the volume up to 50 cm$^3$ with the buffer solution of pH 3.5.

The procedure is as follows: 250 mg of dry hair to be studied, the approximate length of which is 2 cm, are weighed to within 1 mg (the term dry hair being understood as meaning hair in equilibrium with the ambient humidity).

The sample of hair is introduced into a test tube, and 5 cm$^3$ of the dilute solution of "Violet Ext D and C" referred to under (c) are added thereto. The tube is closed immediately with a plug, and shaken by hand for 1 minute.

After one minute, the contents are filtered rapidly on a glass frit and the filtrate is collected; a 2 cm$^3$ sample of the filtrate is taken and diluted in a 10 cm$^3$ calibrated flask with the buffer solution of pH 3.5; the concentration of acidic dyestuff in the dilute solution obtained from the filtrate is measured on a "BECKMAN" type spectrophotometer equipped with a glass cell having an optical path of 10 mm. The absorbance $A_x$ is measured at 560 nm.

The results are expressed per the following Equation, wherein $A_x$ is presumed to be the absorbance of the dilute solution obtained from the filtrate which has acted on the hair, and $A_o$ is presumed to be the absorbance of the solution (c) of "Violet Ext D and C", diluted under the same conditions as the filtrate, the percentage of acidic dyestuff absorbed then being:

$$I^{(+)}\% = 100\left(1 - \frac{A_x}{A_o}\right)$$

EXAMPLE 7: Method for the spectrophotometric determination of the amount of basic dyestuff adsorbed by hair.

The following reagents are prepared:
(a) Concentrated solution of the dyestuff "Codex Methylene Blue" (number 52.015 in the "Color Index"): 100 mg of dyestuff in 100 cm$^3$ of water; and
(b) dilute solution of "Codex Methylene Blue", obtained by successively introducing 5 cm$^3$ of the colored solution referred to under (a), 20 cm$^3$ of a 0.1 N standardised solution of HCl and 20 cm$^3$ of a 0.1 N solution of NaCl into a 100 cm$^3$ calibrated flask and by making the volume up to 100 cm$^3$ with water which has been passed twice through an exchanger.

The procedure is as follows: 250 mg of dry hair, the approximate length of which is 2 cm, are weighed to within 1 mg. The sample of hair is introduced into a test tube, and 5 cm$^3$ of the dilute solution of methylene blue referred to under (b) are added thereto. The tube is closed immediately with a plug and shaken by hand for 2 minutes.

After 2 minutes, the contents are filtered rapidly on a glass frit and the filtrate is collected; a 1 cm$^3$ sample of the filtrate is taken, 2 cm$^3$ of a 0.1 N standardised solution of HCl and 2 cm$^3$ of a 0.1 N solution of NaCl are added thereto and the volume is then made up to 10 cm$^3$ with water which has been passed twice through an exchanger. The spectrophotometer used is the same as above. The absorbance $A_x$ is measured at 660 nm.

The results are expressed as follows: if $A_x$ is the absorbance of the dilute solution obtained from the filtrate which has acted on the hair, and $A_o$ is the absorbance of the solution of "Methylene Blue", referred to under (b) and diluted under the same conditions as the filtrate, the percentage of basic dyestuff absorbed is then:

$$I^{(-)}\% = 100\left(1 - \frac{A_x}{A_o}\right)$$

It has been found that the two methods of spectrophotometric determination described above make it possible to evaluate, precisely and reliably, the degree of charge on a hair which has undergone a cosmetic treatment such as, for example, a permanent-waving, a bleaching or a dyeing treatment, involving a cationic polymer which has modified the ionic state of the hair.

TABLE I

List of the acidic dyestuffs which can be used in the process for evaluating the ionic state of the hair

| Type of dyestuff | Formula | No. in "Color Index" |
|---|---|---|
| AZO | | |
| Red No. 4 FDC | [structure] | 14.700 |
| KITON FAST RED R | [structure] | 14.905 |
| TRIPHENYLMETHANE | | |
| Acid Blue 7 | [structure] | 42.080 |
| PHTHALOCYANINE | | |
| Ariabel Blue 14-12 | [structure] | 74.220 |
| AZINE | | |
| Nigrosine CBRS | No formula in the "Color Index" | 50.420 |
| ANTHRAQUINONE | | |
| Violet Ext D and C | [structure] | 60.730 |

TABLE I-continued
List of the acidic dyestuffs which can be used in the process for evaluating the ionic state of the hair

| Type of dyestuff | Formula | No. in "Color Index" |
|---|---|---|
| Green No. 5 D and C | (anthraquinone with two NH-aryl groups bearing SO₃Na and CH₃ substituents) | 61.570 |
| ANTHRAQUINONE (fluorescent) Green D and C No. 8 | (pyrene trisulfonate with OH group: NaO₃S, SO₃Na, NaO₃S, OH) | 59.040 |

TABLE II
List of the basic dyestuffs which can be used in the process for evaluating the ionic state of the hair

| Type of dyestuff | Formula | No. in the "Color Index" |
|---|---|---|
| ANTHRAQUINONE Quaternary | anthraquinone with $NH(CH_2)_3N(CH_3)_3^{\oplus}$ and $(CH_3)_3N^{\oplus}(CH_2)_3NH$ substituents · 2 $CH_3SO_4^{\ominus}$ | |
| | anthraquinone with $NH(CH_2)_2N^{\oplus}(C_2H_5)_2CH_3$ substituent · $CH_3SO_4^{\ominus}$ | |
| Secondary | anthraquinone with $NH(CH_2)_3NHCH_2CH_2OH$ and $OH$ substituents | |
| Primary | anthraquinone with $NH(CH_2)_3NH_2$ and $NHCH_3$ substituents | |
| AZO Chrysoidine R | phenyl-N=N-(diaminotoluene with NH₂, NH₂, CH₃) | 11.320 |
| THIAZINE Codex Methylene Blue | $(CH_3)_2N^{\oplus}$=⟨phenothiazine⟩-$N(CH_3)_2$, $Cl^{\ominus}$ | 52.015 |

TABLE II-continued

List of the basic dyestuffs which can be used in the process for evaluating the ionic state of the hair

| Type of dyestuff | Formula | No. in the "Color Index" |
|---|---|---|
| XANTHENE DERIVATIVE | | |
| (fluorescent) Rhodamine B extra base | $(H_5C_2)_2N\text{-}[\text{ring}]\text{-}O\text{-}[\text{ring}]=N(C_2H_5)_2Cl^{\ominus}$, with $C=[\text{ring}]\text{-}COOH$ | 45.170 |

TABLE III

Neutral dyestuffs which can be used in the process for evaluating the ionic state of the hair

| Type of dyestuff | Formula | No. in the "Color Index" |
|---|---|---|
| Nitrobenzene derivative | $NH_2$, $NO_2$, $NH_2$ (on benzene ring) | 76.070 |
| Nitrobenzene derivative | $NHCH_2CH_2OH$, $NO_2$, $OH$ (on benzene ring) | |

We claim:

1. A process for evaluating the ionic state of keratin fibers with particular respect to the surface thereof, which process comprises:

taking samples having a weight between about 10 mg. and about 50 mg. of fibers from the fibers to be evaluated; then contacting at a temperature of about normal room or other ambient temperature the said fiber samples with:

a set of at least two solutions of dyestuff, each of which is placed in contact with a sample of the fibers, one of said two solutions containing at least one acidic dyestuff and being capable of changing its coloration in the presence of fibers in the (+) ionic state, and the other of said two solutions containing at least one basic dyestuff and being capable of changing its coloration in the presence of fibers in the (−) ionic state, the pH of the two solutions being such that the initial coloration of each solution remains unchanged in the presence of fibers in the neutral ionic state; and the solution capable of changing its coloration in the presence of fibers in the (+) ionic state containing two acidic dyestuffs giving different colorations; and each of said solutions in any given combination set thereof being in volume in a quantity that is between about 0.25 cm.$^3$ and about 1 cm.$^3$ with the dyestuff concentration in each of said solutions being on the order of between about 0.005% by weight and about 0.03% by weight; and thereafter observing what, if any, change in the color of the solutions has occurred; and finally deducing by color comparison the ionic state of at least the surface of said fibers according to the detectable change in coloration of said involved sets of dyestuff solutions.

2. A process for evaluating the ionic state of keratin fibers with particular respect to the surface thereof, which process comprises:

taking samples having a weight between about 10 mg. and about 50 mg. of fibers from the fibers to be evaluated; then contacting at a temperature of about normal room or other ambient temperature the said fiber samples with:

a set of at least two solutions of dyestuff, each of which is placed in contact with a sample of the fibers, one of said two solutions containing an acidic dyestuff and a neutral dyestuff and being capable of changing its coloration in the presence of fibers in the (+) ionic state, and the other of said two solutions containing at least one basic dyestuff and being capable of changing its coloration in the presence of fibers in the (−) ionic state, the pH of the two solutions being such that the initial coloration of each solution remains unchanged in the presence of fibers in the neutral ionic state; and the solution capable of changing its coloration in the presence of fibers in the (+) ionic state containing an acidic dyestuff and a neutral dyestuff giving different colorations; and each of said solutions in any given combination set thereof being in volume in a quantity that is between about 0.25 cm.$^3$ and about 1 cm.$^3$ with the dyestuff concentration in each of said solutions being on the order of between about 0.005% by weight and about 0.03% by weight; and thereafter observing what, if any, change in the color of the solutions has occurred; and finally deducing by color comparison the ionic state of at least the surface of said fibers according to the detectable change in coloration of said involved sets of dyestuff solutions.

3. A process for evaluating the ionic state of keratin fibers with particular respect to the surface thereof, which process comprises:

taking samples having a weight between about 10 mg. and about 50 mg. of fibers from the fibers to be evaluated; then contacting at a temperature of about normal room or other ambient temperature the said fibers with:

a set of at least two solutions of dyestuff, each of which is placed in contact with a sample of the fibers,
one of said two solutions containing at least one acidic dyestuff and being capable of changing its coloration in the presence of fibers in the (+) ionic state, and
the other of said two solutions containing at least one basic dyestuff and being capable of changing its coloration in the presence of fibers in the (−) ionic state,
the pH of the two solutions being such that the initial coloration of each solution remains unchanged in the presence of fibers in the neutral ionic state; and
the solution capable of changing its coloration in the presence of fibers in the (−) ionic state containing two basic dyestuffs giving different colorations; and
each of said solutions in any given combination set thereof being in volume in a quantity that is between about 0.25 cm.$^3$ and about 1 cm.$^3$ with the dyestuff concentration in each of said solutions being on the order of between about 0.005% by weight and about 0.03% by weight; and thereafter
observing what, if any, change in the color of the solutions has occurred; and finally
deducing by color comparison the ionic state of at least the surface of said fibers according to the detectable change in coloration of said involved sets of dyestuff solutions.

4. A process for evaluating the ionic state of keratin fibers with particular respect to the surface thereof, which process comprises:
taking samples having a weight between about 10 mg. and about 50 mg. of fibers from the fibers to be evaluated; then
contacting at a temperature of about normal room or other ambient temperature the said fibers with:
a set of at least two solutions of dyestuff, each of which is placed in contact with a sample of the fibers,
one of said two solutions containing at least one acidic dyestuff and being capable of changing its coloration in the presence of fibers in the (+) ionic state, and
the other of said two solutions containing a basic dyestuff and a neutral dyestuff and being capable of changing its coloration in the presence of fibers in the (−) ionic state,
the pH of the two solutions being such that the initial coloration of each solution remains unchanged in the presence of fibers in the neutral ionic state; and
the solution capable of changing its coloration in the presence of fibers in the (−) ionic state containing a basic dyestuff and a neutral dyestuff giving different colorations; and
each of said solutions in any given combination set thereof being in volume in a quantity that is between about 0.25 cm.$^3$ and about 1 cm.$^3$ with the dyestuff concentration in each of said solutions being on the order of between about 0.005% by weight and about 0.03% by weight; and thereafter
observing what, if any, change in the color of the solutions has occurred; and finally
deducing by color comparison the ionic state of at least the surface of said fibers according to the detectable change in coloration of said involved sets of dyestuff solutions.

5. A process in accordance with any one of the processes of claims 1, 2, 3 or 4, which process is conducted for evaluating the ionic state of the surface of human hair.

6. The process of claim 5, wherein the said samples of human hair taken are those human hair samples which have previously been washed with a non-ionic detergent solution.

7. A process in accordance with any one of the processes of claims 1, 2, 3 or 4, wherein the said samples of fibers taken are those fiber samples which have previously been washed with a non-ionic detergent solution.

8. A process in accordance with any one of the processes of claims 1, 2, 3 or 4, wherein said fiber samples are placed in contact with the said solutions for a period of between about 30 seconds and about 3 minutes in time.

9. The process of claim 1, wherein said solution that is capable of changing its coloration in the presence of fibers in the (+) ionic state contains a mixture of phthalocyanine and "Kiton Fast Red R".

10. The process of claim 2, wherein said solution that is capable of changing its coloration in the presence of fibers in the (+) ionic state contains a mixture of "Violet Ext D and C" as the acidic dyestuff and, as the neutral dyestuff, 3-nitro-4-N-(β-hydroxyethyl)-aminophenyl.

11. A process in accordance with either one of the processes of claims 3 or 4, wherein at least one of the basic dyestuffs involved in the said solution that is capable of changing its coloration in the presence of fibers in the (−) ionic state is an anthraquinone dyestuff having a quaternary ammonium group or a secondary or primary amine group therein that is selected from the Group consisting of "Chrysoidine R", "Codex Methylene Blue" and "Rhodamine B extra base".

12. The process of claim 3, wherein said solution that is capable of changing its coloration in the presence of fibers in the (−) ionic state contains a mixture of "Astracyanine B" and "Deorline Brilliant Red 4G".

13. The process of claim 4, wherein said solution that is capable of changing its coloration in the presence of fibers in the (−) ionic state contains a mixture of 1-N-(γ-aminopropyl)-amino-4-N'-(methyl)-aminoanthraquinone as the basic dyestuff and, as the neutral dyestuff, 2-nitro-para-phenylenediamine.

14. A process in accordance with any one of the processes of claims 1, 2, 3, 4, 9, 10, 12 or 13, wherein the change in the color of the solution capable of changing its coloration is evaluated by visual color comparison.

15. A process in accordance with that of claim 11, wherein the change in the color of the solution capable of changing its coloration is evaluated by visual color comparison.

16. A process in accordance with either one of the processes of claims 1 or 2, wherein
the change in the color of the solution capable of changing its coloration is evaluated by spectrophotometric means; and
said solution which possibilitates such determination spectrophotometrically of the degree of (+) charge in the ionic state of the fibers being tested has a pH of about 3.5 and contains therein the acidic dyestuff "Violet Ext D and C".

17. A process in accordance with that of claim 16, wherein said fiber samples which are taken are those fiber samples which have previously been washed with a non-ionic detergent solution.

18. Testing the ionic state of the surface of human hair by a process which is in accordance with that of claim 17.

19. A process in accordance with either one of the processes of claims 3 or 4, wherein the change in the color of the solution capable of changing its coloration is evaluated by spectrophotometric means; and said solution which possibilitates such determination spectrophotometrically of the degree of (−) charge in the ionic state of the fibers being tested has a pH of about 1.8 and contains therein the basic dyestuff "Codex Methylene Blue".

20. A process in accordance with that of claim 19, wherein said fiber samples which are taken are those fiber samples which have previously been washed with a non-ionic detergent solution.

21. Testing the ionic state of the surface of human hair by a process which is in accordance with that of claim 20.

* * * * *